United States Patent [19]

Heller

[11] Patent Number: 4,567,881
[45] Date of Patent: Feb. 4, 1986

[54] COMBINATION OTOSCOPE AND AUDIOMETER
[75] Inventor: James W. Heller, Camillus, N.Y.
[73] Assignee: Welch Allyn Inc., Skaneateles Falls, N.Y.
[21] Appl. No.: 480,940
[22] Filed: Mar. 31, 1983
[51] Int. Cl.$^4$ .............................................. A61B 1/22
[52] U.S. Cl. ........................................ 128/9; 128/746
[58] Field of Search .................. 128/9, 419 PS, 746; 242/186

[56] References Cited

U.S. PATENT DOCUMENTS

| | | | |
|---|---|---|---|
| 3,105,876 | 10/1963 | Mullin et al. | 128/746 |
| 3,588,358 | 6/1971 | Rednose | 128/746 |
| 3,698,387 | 10/1972 | Moore et al. | 128/9 |
| 3,799,146 | 3/1974 | John et al. | 128/746 |
| 3,879,756 | 4/1975 | De Bell et al. | 242/186 |
| 3,942,515 | 3/1976 | Servos et al. | 128/746 |
| 3,949,735 | 4/1976 | Klar et al. | 128/746 |
| 4,007,707 | 3/1977 | Ward | 128/746 |
| 4,100,493 | 8/1978 | Procter et al. | 128/9 |
| 4,197,880 | 4/1980 | Schulman et al. | 128/419 PS |
| 4,434,800 | 3/1984 | Anson et al. | 128/746 |

FOREIGN PATENT DOCUMENTS 2408765 9/1975 Fed. Rep. of Germany ...... 128/746

Primary Examiner—Edward M. Coven
Assistant Examiner—Max F. Hindenburg
Attorney, Agent, or Firm—Bruns and Wall

[57] ABSTRACT

A combination otoscope and audiometer provided with conventional lighting means and an unobstructed viewing passage for visually inspecting the ear canal of a patient. The hand held instrument is also provided with a calibrated electronic circuit that automatically produces a sequence of tones of different frequencies and intensities, together with means for transmitting these tones to the patient's ear. The circuit includes timing means for precisely controlling the duration of each tone. Neither the production of the tones nor the duration thereof is under the control of the operator. The exterior of the instrument is provided with indicators in the form of light emitting diodes to tell the operator when each tone is being transmitted to the patient's ear.

6 Claims, 8 Drawing Figures

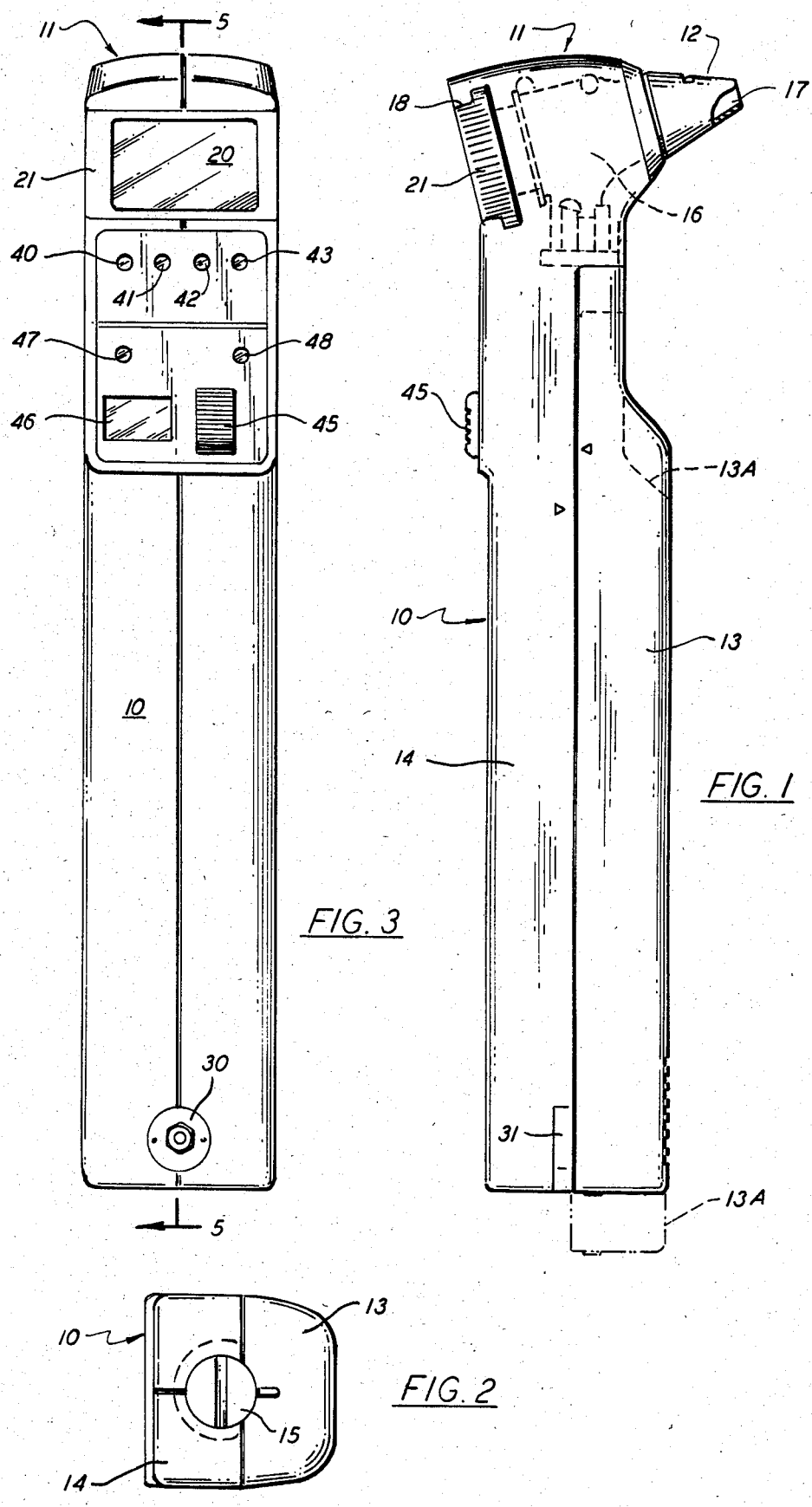

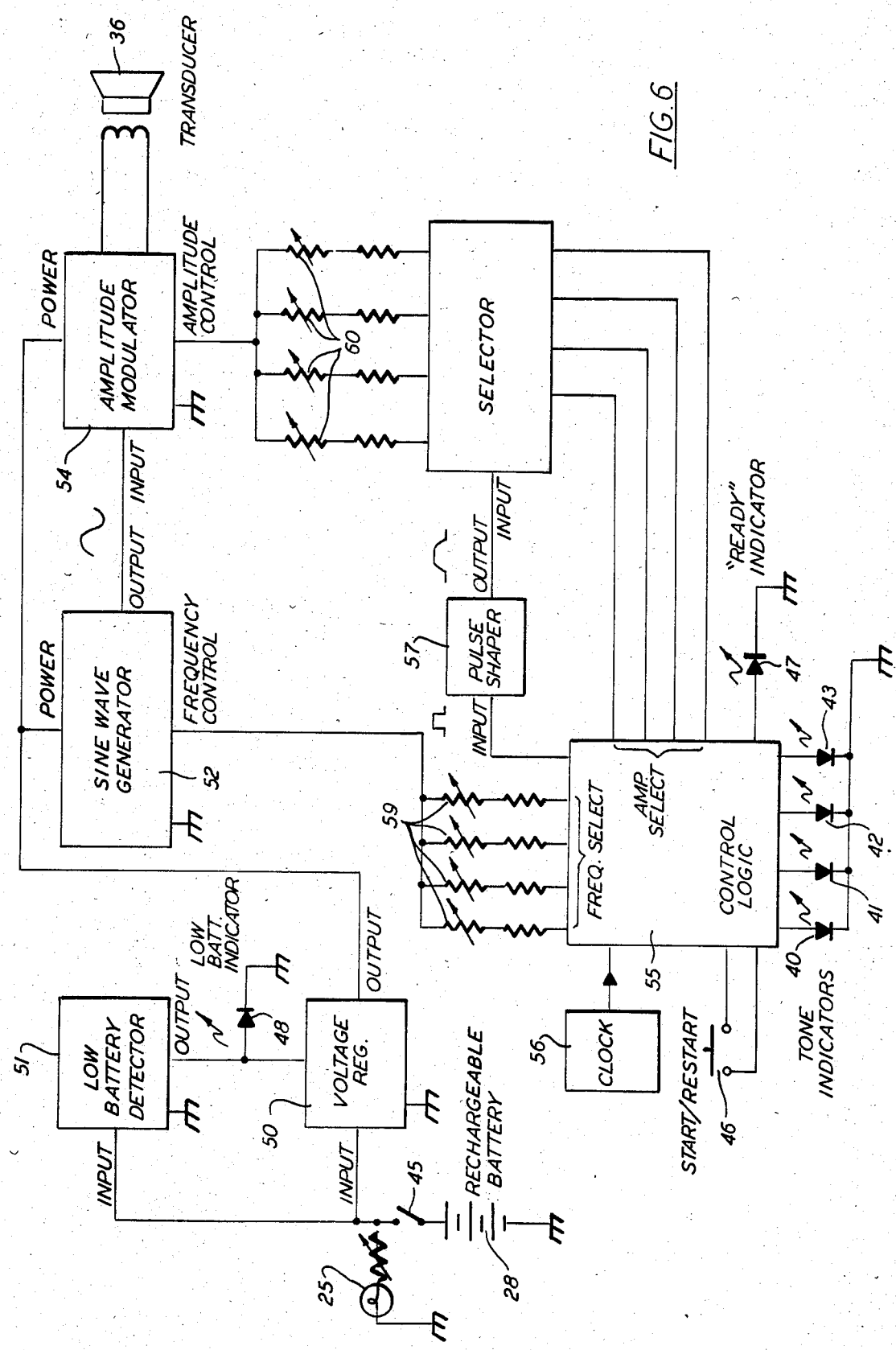

COMBINATION OTOSCOPE AND AUDIOMETER

BACKGROUND OF THE INVENTION

This invention relates generally to medical diagnostic instruments, and has particular reference to a novel audiometer that is incorporated in a hand held otoscope.

Hand held otoscopes of both the diagnostic and operating types are well known in the prior art. Likewise, audiometers for detecting hearing disabilities are well known. Conventional audiometers are not hand held instruments but rather are relatively large table supported units that utilize earphones in testing the patient. In addition, conventional audiometer equipment is usually installed in sound proof cells or the like so that ambient noise is reduced to a minimum.

The only easily portable, hand held audiometer known to the applicant is disclosed in U.S. Pat. No. 3,105,876, issued Oct. 1, 1963 to C. D. Mullin et al. The Mullin apparatus is not a combination instrument as is the present invention and is capable of operating only as a hearing checking device. The Mullin audiometer checks the hearing capabilities of the patient at a plurality of frequency and intensity levels. Unfortunately, the frequencies are changed by manually moving a dial and this in itself creates a noise that can give the patient a clue or a miscue. Another drawback of the Mullin apparatus is that the duration of the audio-frequency signal is apparently under the control of the operator whereas the duration of the signals should be completely uniform and precise for accurate test results.

SUMMARY OF THE INVENTION

Prior to testing the hearing of a patient, proper procedure requires a visual examination of the ear canal to confirm that there is a clear passage to the tympanic membrane. This eliminates the possibility of a false diagnosis because of ear wax or some other obstruction. With conventional audiometric equipment, the initial visual examination requires a separate instrument in the form of a conventional otoscope and this initial step is not always carried out. With the hand held combination instrument of the invention, the initial visual examination and ensuing hearing test can be conducted with the same instrument and both tests can be accomplished without removing the instrument speculum from the patient's ear.

The combination otoscope and audiometer of the invention is provided with conventional lighting means and an unobstructed viewing passage for visually inspecting the ear canal of the patient. In addition, the instrument is provided with a calibrated electronic circuit that automatically produces a sequence of tones of different frequencies, together with means for transmitting these tones to the patient's ear. The circuit also includes timing means for precisely controlling the duration of each tone. Neither the production of the tones nor the duration thereof is under the control of the operator.

The exterior of the combination otoscope and audiometer is provided with indicators preferably in the form of light emitting diodes to tell the operator when each tone is being transmitted to the patient's ear. In addition, the instrument has control switches, a "Ready" indicator and a low battery indicator, the battery preferably being of the rechargeable type.

BRIEF DESCRIPTION OF THE DRAWINGS

FIG. 1 is a side elevation of a combined otoscope and audiometer embodying the present invention, a portion of the speculum being broken away to better illustrate the construction;

FIG. 2 is a bottom plan view of the instrument of FIG. 1;

FIG. 3 is a rear elevation of the instrument of FIG. 1;

FIG. 6 is a block diagram of the electronic circuitry for the instrument;

DESCRIPTION OF THE PREFERRED EMBODIMENT

Figure 4:
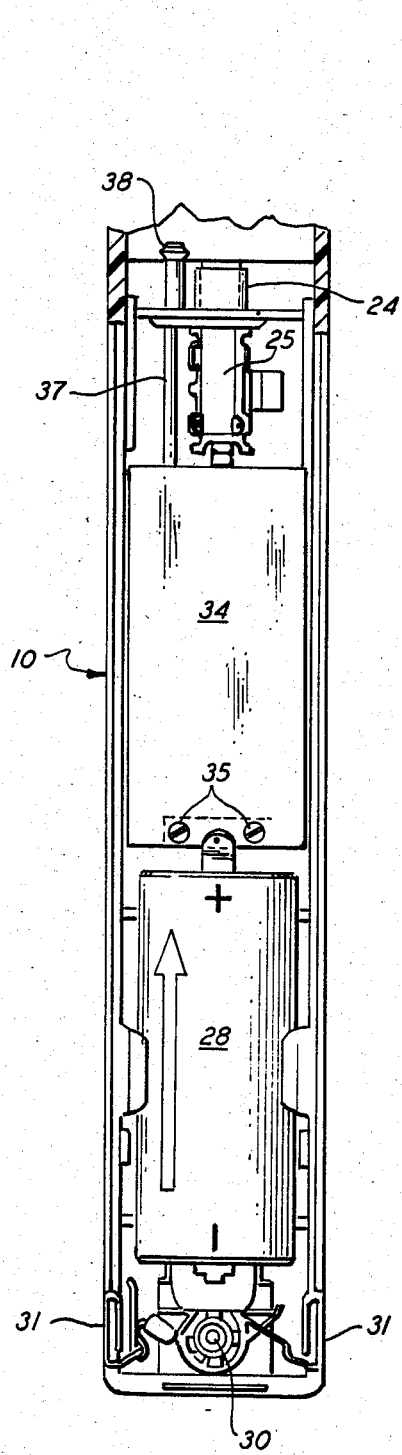
FIG. 4 is a fragmentary front elevation of the instrument with the cover removed to show the arrangement of the internal parts.

Referring now to the drawings, and with particular reference to FIGS. 1-3, the combined otoscope and audiometer disclosed herein is essentially comprised of an elongated body or handle portion 10 and a head portion 11, the latter having an integral speculum 12. The handle is hollow and includes a removable cover 13 that permits access to the interior of the handle. Cover 13 is engaged with and disengaged from the other part 14 of the handle by a longitudinal sliding movement as indicated by the dash lines 13A in FIG. 1. The cover is normally locked in its engaged position by a disc 15, FIG. 2, that is rotatable 180° between locking and unlocked positions.

As is conventional in otoscopes, there is a clear viewing passage 16 through the head portion 11, the passage extending from an opening 17 at the distal end of the speculum 12 to an opening 18 at the rear of the head portion. The opening 18 is normally closed in a substantially airtight manner by a closure member comprised of a lens 20 and frame 21 of the type disclosed in U.S. Pat. No. 3,698,387, issued Oct. 17, 1972 to William C. Moore et al and owned by the assignee of the present invention.

Figure 5:
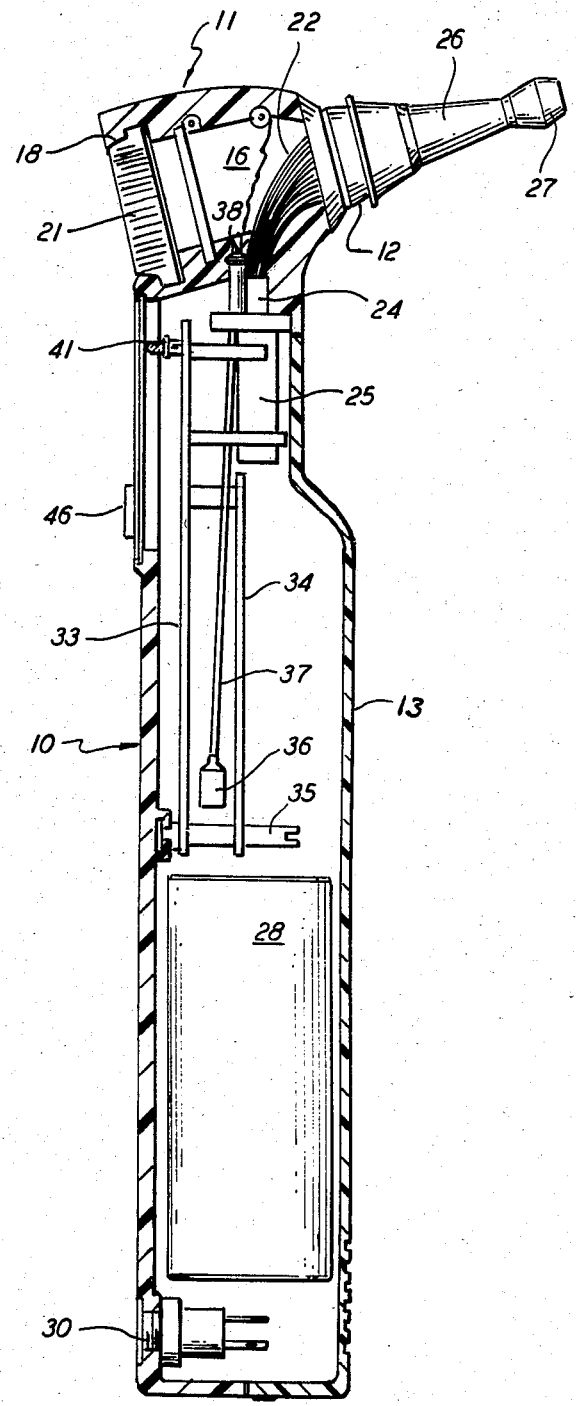
FIG. 5 is a longitudinal section through the instrument taken on line 5—5 of FIG. 3.

The opening 17 at the distal end of the speculum is encircled by a pre-formed bundle 22, FIG. 5, of light transmitting optical fibers that are embedded in the speculum wall. The fiber bundle curves downwardly into the upper end of a sleeve 24 at the upper end of the handle 10. At its light receiving end, the fiber bundle becomes cylindrical. The light emitting end of a lamp 25 is received in the lower end of the sleeve so that the bundle receives light from the lamp and transmits it to the distal end of the speculum where it is emitted in a substantially annular pattern to illuminate the field of view. The fiber bundle arrangement is not considered to be novel per se having been disclosed in U.S. Pat. No. 3,146,775, issued Sept. 1, 1964 and also owned by the assignee of the present invention.

As indicated in FIG. 5, the instrument speculum 12 in use is provided with a detachable hollow tip 26 that forms an extension of the viewing passage 16 in order to protect the fiber ends at the distal end of the speculum and space them from the area under examination. The tip 26 has a rounded or bulbous distal end 27 of relatively soft deformable material so that a good seal can be achieved between the tip and wall of the ear canal for attenuation of ambient noise and to prevent decreasing dB level at the tympanic membrane due to a leak around the tip. A speculum tip having such a construction is disclosed in copending application Ser. No. 222,281, filed Jan. 5, 1981, now U.S. Pat. No. 4,380,998 and also owned by the assignee of the present invention.

The lamp 25 is preferably a 3.5 volt halogen lamp and it receives its power from a rechargeable battery 28, FIG. 4. At the lower end of the handle 10 there is a socket 30, FIGS. 3 and 4, for receiving a jack connected to a conventional direct plug-in transformer (not shown). Alternatively, the instrument may be provided with a known type of charging stand (not shown) and has external charging contacts 31, FIG. 4, for use with such a stand.

In accord with the invention, the combined otoscope and audiometer includes circuit means for automatically producing in sequence four pure tones of different frequencies, FIGS. 4–6. These tones are used to determine if the person being examined has a hearing disability. The circuits are carried by two printed circuit boards 33 and 34, FIG. 5, that are releasably secured in the interior of the handle by mounting screws 35. The tones produced by the circuit are emitted from a transducer 36 and are carried up into the interior of the head 11 by a sound tube 37, the upper end of the tube being connected to the head by an acoustic coupling 38. From the interior of the head, which has a predetermined volume, the tones pass through the speculum 12 and tip 26 into the ear canal of the patient.

In a preferred embodiment of the invention, the tones produced by the circuit have frequencies of 500 Hz., 1000 Hz., 2000 Hz. and 4000 Hz. and each is at the accepted "normal" hearing threshold of 25 dB. For each tone there is a visual indicator in the form of a light emitting diode, these diodes being shown at 40–43 in FIGS. 3 and 6. As shown in FIG. 3, the instrument also has an ON/OFF switch 45, a START/RESTART switch 46, a READY indicator 47 and a LOW BATTERY indicator 48.

Having reference now to the block diagram of FIG. 6, the entire circuit is powered by the rechargeable battery 28 which is placed in the circuit by closing the ON/OFF switch 45. When switch 45 closes, the halogen lamp 25 lights and the instrument is ready for use as an otoscope. The battery output is controlled by a voltage regulator 50, and a comparator circuit 51 is used to sense low battery voltage. In the event that the battery voltage falls below a predetermined level the indicator 48 is turned on and the remainder of the circuit made inoperative. This prevents inaccurate test results due to inadequate battery voltage.

Upon closing switch 45, a signal is produced by a precision sine wave generator 52 having a single-component frequency control mechanism. The signal is amplitude modulated by an operational transconductance amplifier 54 with controllable gain. The amplifier drives the transducer 36.

When the instrument is to be used as an audiometer, the START/RESTART switch 46 is depressed and this activates a digital sequencing circuit 55 controlled by a clock 56. The sequencing circuit 55 controls the frequency of generator 52 and the gain of the amplifier 54. The sequencing circuit also drives the visual tone indicators 40–43 for the different tones and the READY indicator 47.

A current-source type, square to triangular wave converter 57 is employed to change the control signals from the sequencing circuit 55 into ramp type signals for amplitude control. The converter 57 thus functions as a timing device by controlling in a precise manner the rise and fall times required for the audiometric test tones. While the circuit shown in FIG. 6 will be factory calibrated to produce precise, predetermined frequency and dB levels, it will be apparent that the levels can be changed up or down by a factory technician by changing the values of a few of the components as, for example, the variable resistors shown at 59 for frequency and at 60 for amplitude of the respective frequencies. Alternatively, resistors 59 could be eliminated and the frequency set by a stable, digitally generated frequency control signal with a sine wave generator that locks onto a digital signal.

Figure 7:
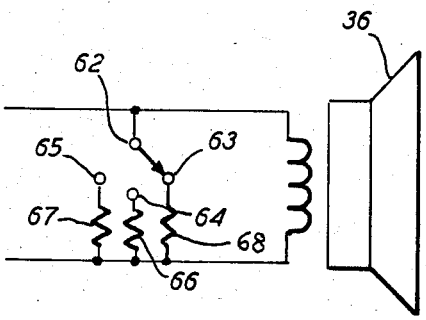
FIG. 7 is a fragmentary portion of the block diagram of FIG. 6 showing a modification in the circuit.

While it was stated above that the four tones of different frequencies are at the accepted "normal" hearing threshold of 25 dB, it may be desirable or necessary to have the tones at higher dB levels as, for example, at 40 dB and 60 dB. To this end, the circuit of FIG. 6 can be modified as shown in FIG. 7 by placing a three position switch 62 across the transducer. With this switch in its first position 63, the tones would be at 25 dB and with the switch in its second and third positions 64 and 65, the tones would be at 40 dB and 60 dB, respectively. The three switch positions introduce resistors 66, 67 and 68 of predetermined values into the circuit.

The instrument described above can be used as a completely self-contained diagnostic otoscope and/or as a screening audiometer. It is suitable for use by the general practitioner, pediatrician, otolaryngologist or his office nurse. The instrument operates effectively under the ambient noise conditions found in a typical, "quiet" office because of the noise attenuation feature of the soft tips which is a significant improvement over standard audiometric headphones. For noisier environments, disposable noise-attenuating ear plugs or single supra-aural cushions can be used in/on the ear not being tested. The instrument can be used for any communicative, cooperative patient of at least four years of age.

As previously noted, in using the combination instrument of the invention, it is first employed as an otoscope to visually examine the ear canal and confirm that there is a clear passage to the tympanic membrane. If there is not a clear path to the tympanic membrane, the sound level at the membrane will not necessarily be accurate. This visualization also assures proper alignment of the tip within the ear canal, thereby eliminating the possibility of sound level variations caused by pointing the tip into the ear canal wall. Also, the tip may serve to expand a collapsed ear canal which may have caused an attenuation of sound level at the tympanic membrane, thus creating a false evaluation of the actual hearing potential of the subject. Any ear wax that is found should, of course, be cleaned out manually. Thereafter, the hearing test can be initiated by depressing the START switch 46.

Before initiating the hearing test, the patient is instructed to raise and lower a finger or perform some other action, when he hears a tone start and stop. The accuracy of the patient's responses can be checked by the examiner as he watches the visual tone indicators 40–43 go on and off. If a patient is unable to hear one or more of the tones, he would normally be referred to a specialist for a complete audiometric evaluation.

It should be noted that switch 46, FIG. 6, is a START/RESTART switch which means that, utilizing conventional circuitry, it can be depressed at any point during the four tone sequence and the sequence will start over. This conceivably could be of assistance to one testing a patient who seems to be trying to "second guess" the system.

The printed circuit boards 33 and 34, transducer 36 and sound tube 37 are all part of a module that can be easily snapped into and out of the instrument upon removing the mounting screws 35. The module is initially calibrated at the factory and can be returned to the factory as necessary to be recalibrated. This can be done in a very short period of time and is far less expensive than a service call. Because all of the modules for these instruments are identical to one another, a good seal is always assured between the acoustic coupling 38 at the upper end of the sound tube, FIG. 5, and the mating conical opening in the head portion into which the coupling is resiliently pressed.

The instrument head 11 is precisely molded and since the same molds are employed for all the instruments manufactured, the volume and geometry of the internal cavities 16 in all the instruments are the same. This, together with uniform calibration of the electronic modules, means that there will be virtually no sound level variations from instrument to instrument.

Figure 8:
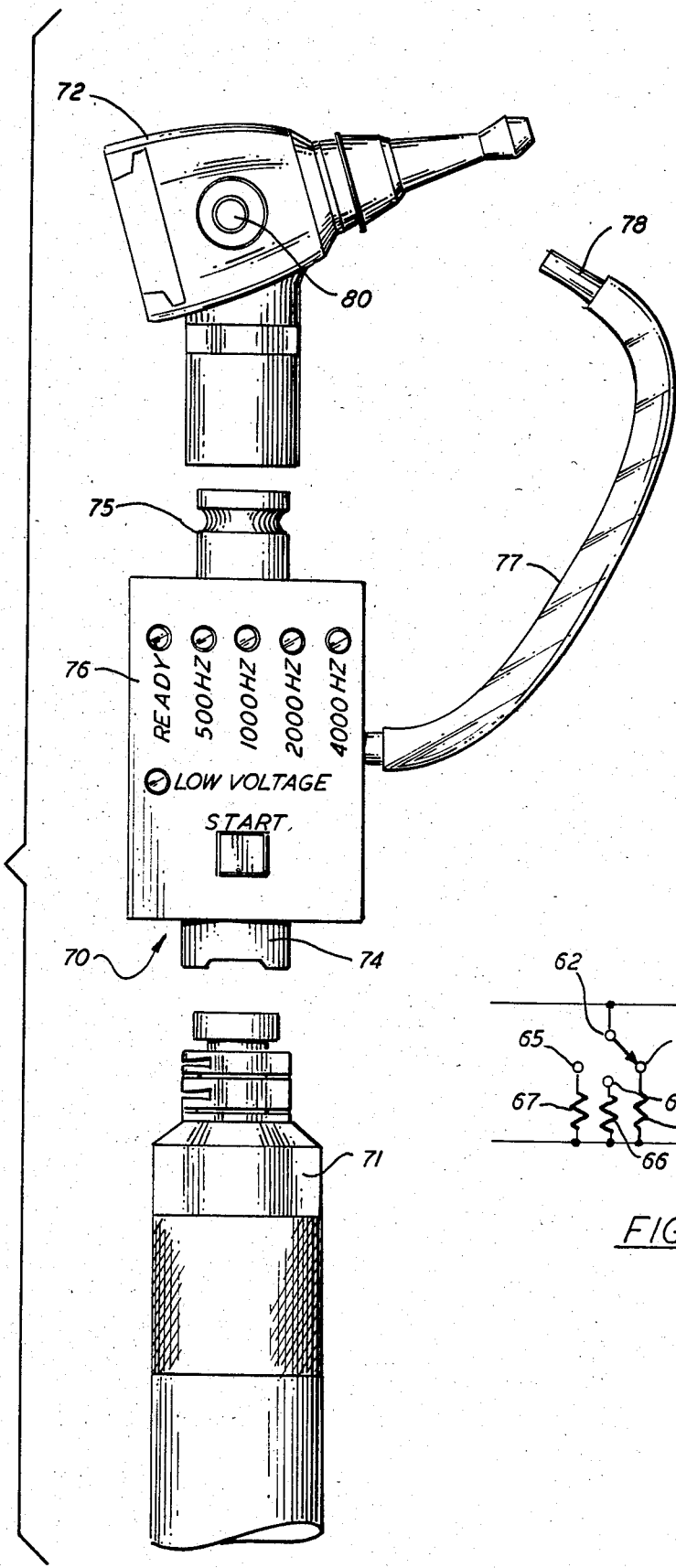
FIG. 8 is an exploded view of a modified form of the instrument of the invention.

FIG. 8 illustrates a modified form of the instrument of the invention wherein an audiometer conversion unit 70 is incorporated in a conventional diagnostic otoscope to provide the combination otoscope and audiometer. The conventional otoscope includes a battery handle 71 and separable otoscope head 72, and the conversion unit is provided with suitable fittings 74 and 75 for engagement with the handle and head respectively. The conversion unit corresponds to the body portion 10 previously described and includes the circuitry described above for producing four tones of different frequencies. The unit is also provided with the same switches and indicators collectively indicated at 76. The ON/OFF switch is provided in the handle 71.

The tones produced by the conversion unit 70 are emitted from a transducer (not shown) like transducer 36 and the transducer is acoustically connected by means of a flexible conduit 77 to the otoscope head 72. At its outer end, the conduit 77 has a fitting 78 that is received in an airtight manner in a hole 80 in the head, the hole being a conventional fitting that permits an inflation bulb to be connected to the otoscope.

From the foregoing description it will be apparent that a novel and highly advantageous medical instrument has been provided by the invention. As will be understood by those familiar with the art, the invention may be embodied in other specific forms without departing from the spirit or essential characteristics thereof.

I claim:

1. A hand held medical instrument in the form of a combined otoscope and audiometer, the instrument having the capability of functioning as an otoscope to confirm that there is a clear passage for the transmission of sound through the canal of the ear being examined and thereafter of functioning as an audiometer for gauging the acuity of hearing, the instrument comprising a body portion and a head portion connected to the body portion, the head portion having an integral speculum, the head portion and speculum having an unobstructed viewing passage therethrough, means in the head portion for directing light rays outwardly into the ear canal, circuit means in the body portion for automatically producing in sequence tones of different frequencies, the circuit means including timing means for precisely controlling the duration of each tone, means including a transducer for transmitting said tones from the body portion to the interior of the head portion from which they pass through the speculum into the ear canal, and means for visually indicating when each tone is produced by the circuit means.

2. A medical instrument as defined in claim 1 wherein the body portion is a conversion unit that is interposed between a conventional otoscope head and a conventional battery handle.

3. A medical instrument as defined in claim 1 together with means in the body portion for producing tones of different intensities.

4. A medical instrument as defined in claim 1 together with means at the distal end of the speculum for effecting a seal between the speculum and ear canal.

5. A medical instrument as defined in claim 1 wherein the circuit means is in the form of a removable and replaceable module that is factory calibrated.

6. A medical instrument as defined in claim 1 together with a battery for supplying power to the circuit means, the circuit means including a low battery indicator and means to render the circuit inoperative in the event that the battery voltage falls below a predetermined level.

* * * * *